United States Patent [19]

Thomson

[11] Patent Number: 4,640,286
[45] Date of Patent: Feb. 3, 1987

[54] OPTIMIZED NERVE FIBER STIMULATION

[75] Inventor: Thomas H. Thomson, Boulder, Colo.

[73] Assignee: Staodynamics, Inc., Longmont, Colo.

[21] Appl. No.: 667,873

[22] Filed: Nov. 2, 1984

[51] Int. Cl.$^4$ .............................................. A61N 1/36
[52] U.S. Cl. .................................................... 128/421
[58] Field of Search .................. 128/419 PG, 421–423

[56] References Cited

U.S. PATENT DOCUMENTS

| | | | |
|---|---|---|---|
| 2,375,575 | 5/1945 | Morland et al. | 128/421 |
| 2,498,882 | 2/1950 | Fizzell et al. | 128/421 |
| 3,522,811 | 8/1970 | Schwartz et al. | 128/419 C |
| 3,946,745 | 3/1976 | Hsiang-Lai et al. | 128/422 |
| 4,147,171 | 4/1979 | Greene et al. | 128/421 |
| 4,237,899 | 12/1980 | Hagfors et al. | 128/422 |
| 4,256,116 | 3/1981 | Meretsky et al. | 128/421 |
| 4,324,253 | 4/1982 | Greene et al. | 128/421 |

OTHER PUBLICATIONS

Guyton, *Basic Human Neurophysiology–Third Edition*, W. B. Saunders Co., ©1981, pp. 26–28.

*Primary Examiner*—William E. Kamm
*Assistant Examiner*—Mitchell J. Shein
*Attorney, Agent, or Firm*—Robert E. Harris

[57] ABSTRACT

Optimization of nerve fiber stimulation to substantially increase the activity of the then selected nerve fibers is disclosed, with optimization being achieved through utilization of electrical pulses that are caused to occur in a predetermined pattern with respect to polarity, spacing, frequency and duration so as to interact with the electro-neurophysiological characteristics of the particular nerve fibers then to be electrically stimulated. Biphased pulse pairs are repeatedly generated and applied to the nerve fibers to be stimulated with the first pulse of each pulse pair being a positive polarity pulse causing the nerve to be set into the refractory period, while the second pulse of each pulse pair is a negative polarity pulse that is made to occur substantially at the end of the refractory period for the particular nerve fibers then being stimulated to thereby excite those nerve fibers, and the pulse pairs are repeated at a rate based upon the timewise occurrence of the enhanced excitability condition of the nerve fibers then being stimulated. Electrode polarity is absolute, meaning that nerve activity is stimulated almost entirely adjacent to the electrode which has the polarity relationship as above stated. Frequency of occurrence of the pulse pairs and duration of the pulses are preselected to provide a cumulative optimizing effect. Additional normal pulses occurring during the period following occurrence of the first pulse of the pair and before the occurrence of the second pulse of the pair do not normally adversely affect performance, and interleaved pulses can therefore be utilized to simultaneously stimulate a plurality of different types of nerve fibers without adversely affecting optimum stimulation of at least one selected type of the plurality of types of nerve fibers then being stimulated.

25 Claims, 10 Drawing Figures

FLOW CHART FOR MICROCOMPUTER PROGRAM

OPTIMIZED NERVE FIBER STIMULATION

FIELD OF THE INVENTION

This invention relates to electrical nerve fiber stimulation, and, more particularly, relates to optimizing nerve fiber stimulation utilizing bi-phased electrical pulse pairs.

BACKGROUND OF THE INVENTION

It has heretofore been common to electrically stimulate nerves for various therapeutic purposes, and medical practitioners have heretofore used electrical stimulation for stimulating muscle activity, relieving pain, and producing sensation, among other therapeutic purposes.

The sequence of effects produced by electrical stimulation, as its intensity is increased, is known to generally follow a pattern of a perception of an electrical sensation (usually tingling), an increase in sensation, fasciculation muscle contraction, pain, and then injury in the form of electrical burns or cardiac arrhythmias.

While therapeutic effects often occur while stimulation is applied with a continuous intensity below that necessary to produce muscle contraction it should be remembered that exceptions do occur to the general effect pattern such as, for example, when a DC current is applied and slowly increased in intensity, muscle contraction cannot be obtained, though the other effects occur in the same order.

Electrical stimulation has been attempted and/or realized through use of a wide variety of electrical waveforms and these waveforms have ranged from a purely DC (galvanic) current or voltage to many different combinations of electrical pulses of various shapes and durations. While at least some such waveforms have provided some degree of desirable effect, the results achieved have been random with no clear understanding of how optimization might, or could, be achieved.

As brought out hereinabove, stimulation has also been made to occur with many different types of pulses, and pulse pairs that include both positive and negative pulses have heretofore been suggested (see, for example, U.S. Pat. Nos. 2,375,575, 3,946,745, 4,237,899, and 4,256,116). While these patents suggest that bi-phased pulse pairs can be utilized for therapeutic purposes, there is no teaching in these patents of devices or methods that are shown to optimize stimulation. Such optimization is important, however, to achieve results with minimum power and maximum effect on functions of the body controlled by the fibers specifically stimulated.

SUMMARY OF THE INVENTION

This invention provides apparatus and method for achieving optimization of nerve fiber stimulation to thereby increase the overall activity of the nerve fibers then being stimulated. Bi-phased pulse pairs are utilized with the pulses of each pair being separated by a distance, in time, comparable to the refractory period for the particular kinds of nerve fibers then being stimulated, with the frequency of repetition and pulse duration being selected to further enhance stimulation. Moreover, through use of interleaved pulses, a plurality of different types of nerve fibers can be simultaneously stimulated.

It is therefore an object of this invention to provide improved apparatus and method for stimulating nerve fibers.

It is another object of this invention to provide improved apparatus and method for optimizing stimulation of specific kinds of nerve fibers.

It is still another object of this invention to provide improved apparatus and method for optimizing stimulation of nerve fibers to increase the overall activity of such fibers beyond that presently achievable by known stimulating apparatus or methods.

It is yet another object of this invention to provide improved apparatus and method for stimulating nerve fibers utilizing bi-phased pulse pairs.

It is still another object of this invention to provide improved apparatus and method for optimizing stimulation of nerve fibers through use of bi-phased pulse pairs the pulses of each pair of which are spaced a distance, in time, substantially equal to the refractory period for the particular nerve fibers then being stimulated, and with the pulse pairs occurring so as to be timewise spaced from each adjacent pulse pair a distance based upon the timewise occurrence of the enhanced excitability condition of the particular nerve fibers then being stimulated.

It is still another object of this invention to provide improved apparatus and method for stimulating a plurality of different types of nerve fibers utilizing interleaved pulses.

With these and other objects in view, which will become apparent to one skilled in the art as the description proceeds, this invention resides in the novel construction, combination, arrangement of parts and method substantially as hereinafter described, and more particularly defined by the appended claims, it being understood that changes in the precise embodiment of the herein disclosed invention are meant to be included as come within the scope of the claims.

BRIEF DESCRIPTION OF THE DRAWINGS

The accompanying drawings illustrate complete embodiments of the invention according to the best mode so far devised for the practical application of the principles thereof, and in which.

DESCRIPTION OF THE INVENTION

Figure 1:
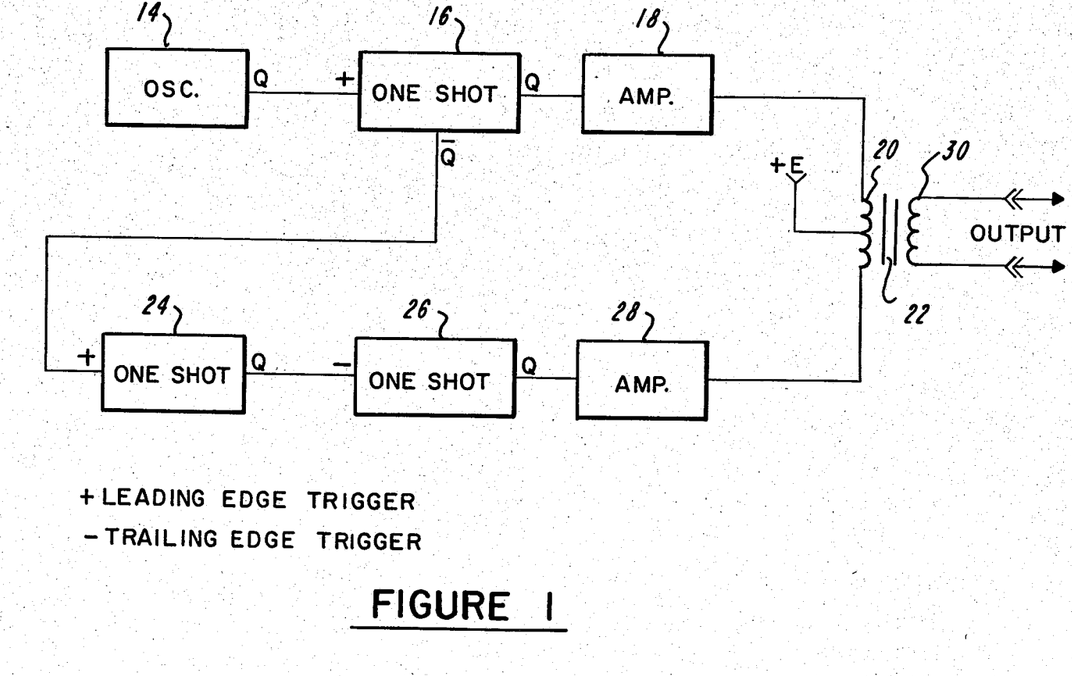
FIG. 1 is a block and schematic diagram of apparatus according to this invention useful for optimizing electrical stimulation of nerve fibers.

The apparatus and method of this invention optimizes electrical stimulation of selected nerve fibers, and an apparatus useful for producing the required pulse pair is shown by the generalized block diagram of FIG. 1.

As shown in FIG. 1, apparatus 12 includes oscillator 14 that provides an input signal to one shot multivibrator 16 to trigger the multivibrator at a leading edge of the input signal from oscillator 14. The Q output from one shot multivibrator 16 is coupled through amplifier 18 to one side of primary winding 20 of transformer 22, while the $\overline{Q}$ output from one shot multivibrator 16 is coupled as an input to one shot multivibrator 24 with a leading edge of this input signal triggering multivibrator 24.

The Q output from one shot multivibrator 24 is coupled to one shot multivibrator 26 with a trailing edge of this input signal triggering multivibrator 26. The output from one shot multivibrator 26 is coupled through amplifier 28 to the other side of primary winding 20 of transformer 22.

Figure 2:
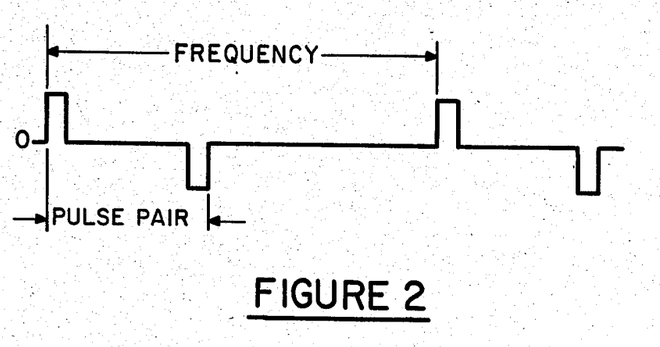
FIG. 2 is a typical representation of bi-phased pulse pairs utilized in this invention.
Figure 9:
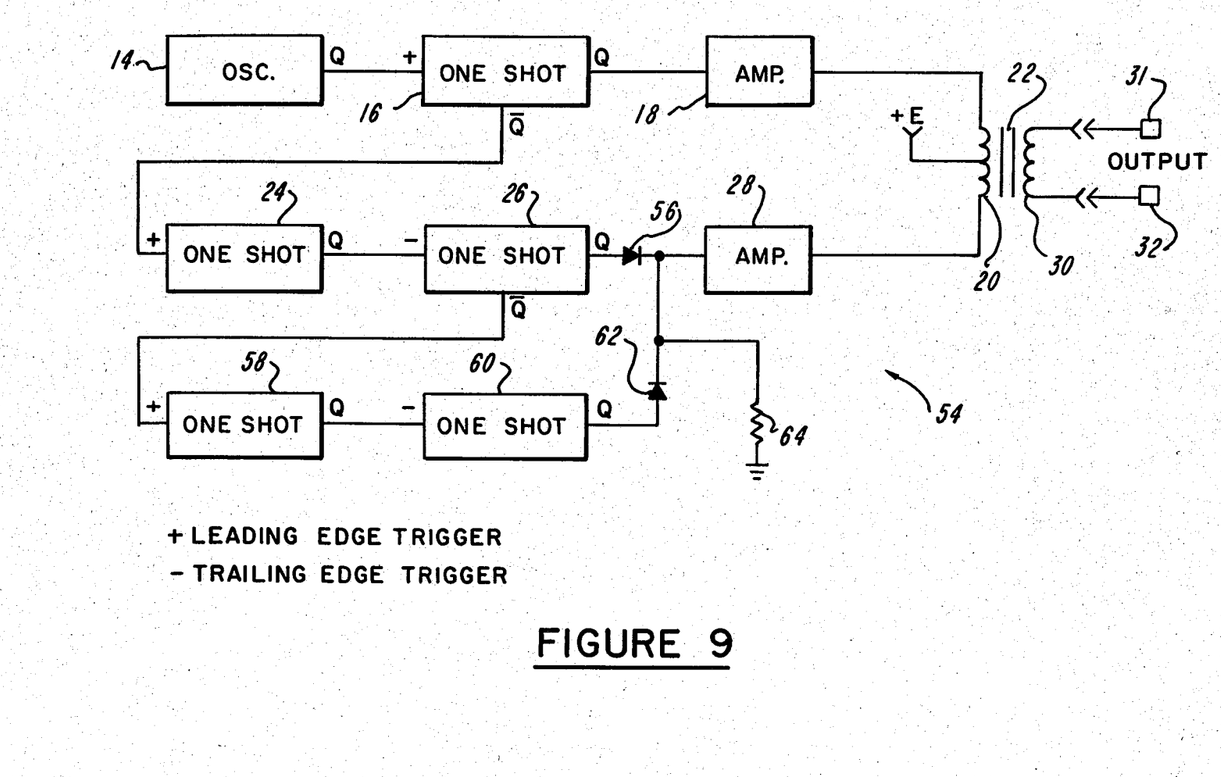
FIG. 9 is a block and schematic diagram of apparatus according to this invention useful for providing interleaved pulse pairs.

The output taken from secondary winding 30 of transformer 22 is a series of pulse pairs which are coupled to electrodes 31 and 32 (as indicated in FIG. 9) for non-invasive application of the pulse pairs to the nerve fibers then selected for stimulation. Typical bi-phased pulse pairs useful in this invention and produced at the output (from secondary winding 30 as shown in FIG. 1) are shown in FIG. 2, with the pulses being spaced, in time, by a distance equal to that of the refractory period in order to optimize performance, as brought out more fully hereinafter.

Figure 3:
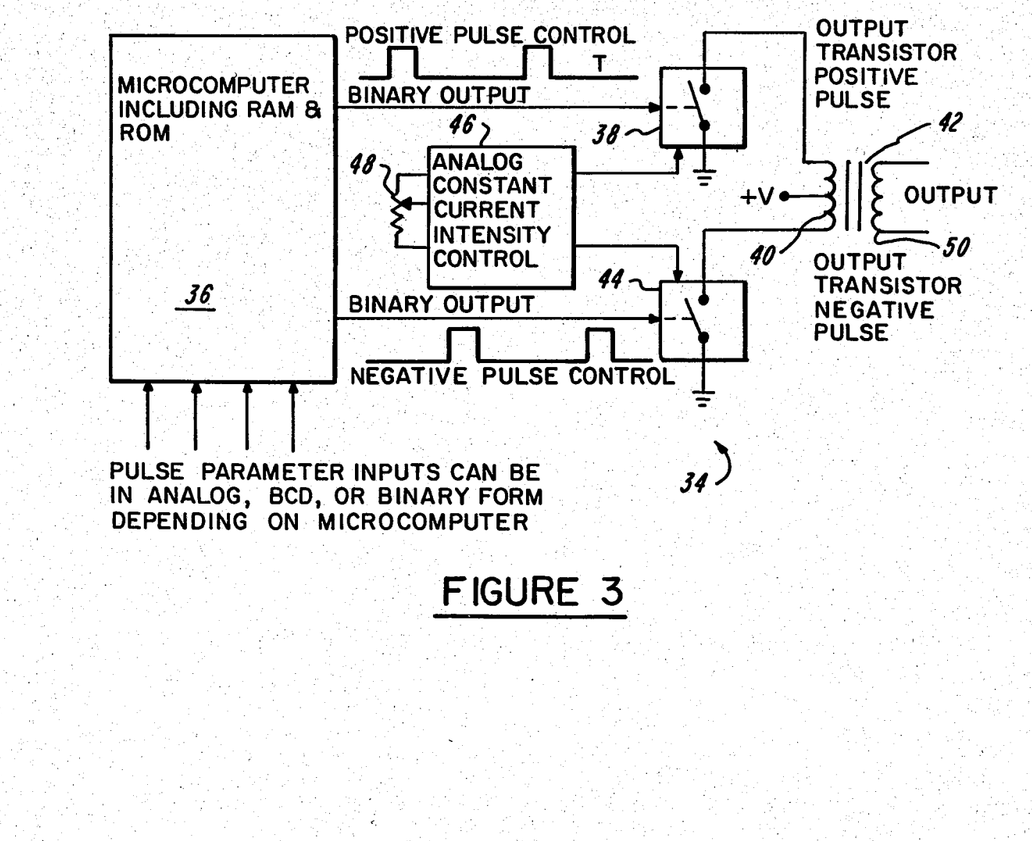
FIG. 3 is a block and schematic diagram of a microcomputer controlled nerve stimulator that can be used for optimizing electrical stimulation of nerve fibers.
Figure 4:
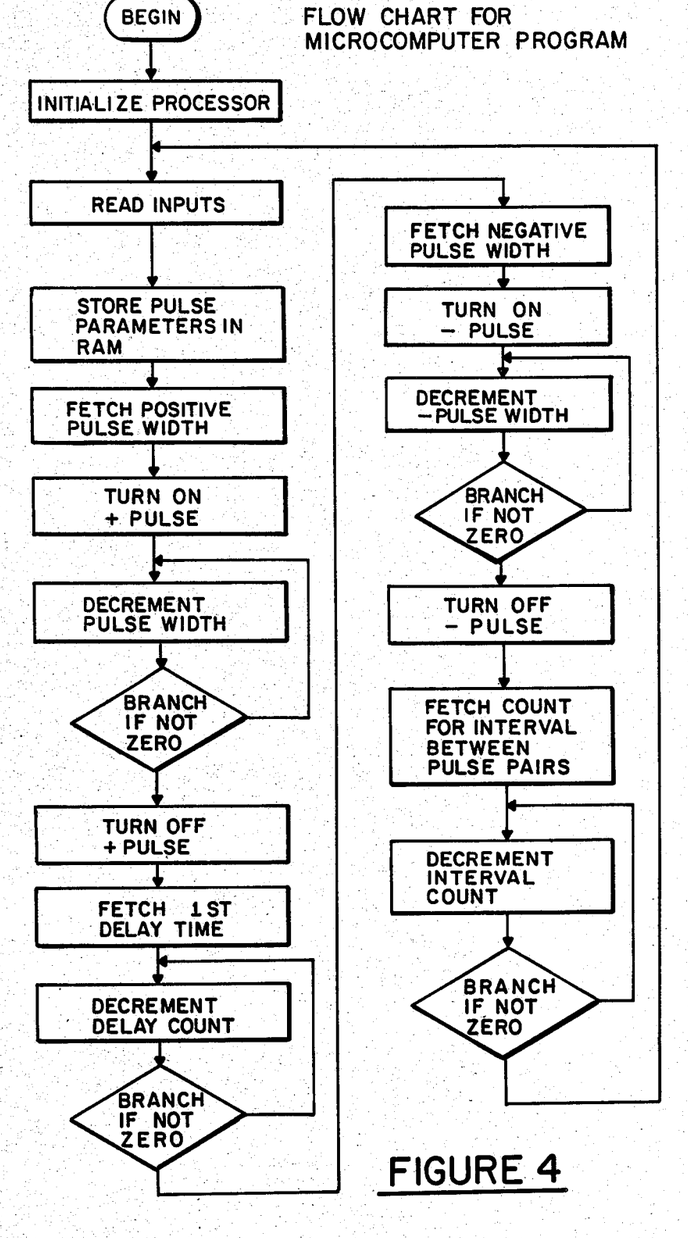
FIG. 4 is a flow chart for the microcomputer program of the microcomputer shown in FIG. 3.

An alternate embodiment 34 of apparatus useful for providing the required pulse pairs is shown as a microcomputer controlled nerve stimulator in FIG. 3. As shown, microcomputer 36 is caused to provide positive output pulses which are coupled through switch 38 to one side of primary winding 40 of transformer 42, and is caused to provide negative output pulses which are coupled through switch 44 to the other side of primary winding 40 of transformer 42. A flow chart for the microcomputer program for microcomputer 36 is shown in FIG. 4.

Switches 38 and 44 are controlled by analog constant current and intensity control 46, having a potentiometer 48 connected therewith, and allow switching of polarity sequences between the electrodes connected with the output from the device to thus achieve optimum stimulation under both electrodes alternately. The output from the device is coupled from secondary winding 50 to electrodes (such as electrodes 31 and 32 as shown in FIG. 9) for non-invasive application of the pulse pair to the nerve fiber then selected for stimulation.

The bi-phased pulse pair provided operates in the same manner as does the bi-phased pulse pair provided by the device as shown in FIG. 1, with the pulses being likewise spaced, in time, by a distance equal to that of the refractory period in order to optimize performance, as brought out more fully hereinafter.

To understand optimization of stimulation according to this invention, the nature and function of nerve fibers should first be understood. Individual nerve cells are called neurons and are contained in cable-like bundles in the nervous tissue called nerves. The individual nerve fibers comprise a portion of a nerve cell extending from the nerve cell body to its end point where the activity for which that neuron is responsible is either detected by the neuron or influenced by the neuron. In peripheral nerves (i.e., those not contained in the spine or skull or in the autonomic nervous system), nerve fibers extend from the spinal cord as a continuous filament to the point where they interact with other tissue.

Nerve fibers conduct information in much the same manner as does a cable, and generally carry information in binary form. The number of nerve pulses per unit time determines the degree of activity since each nerve pulse for a given nerve fiber is identical (for practical purposes) to every other pulse relayed by that fiber.

Figure 5:
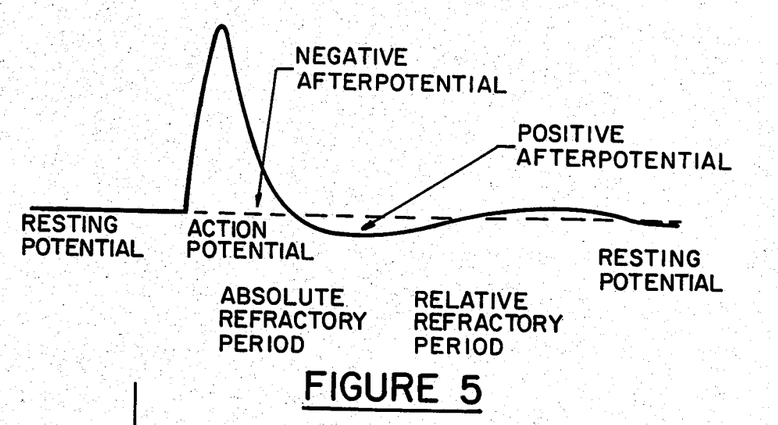
FIG. 5 is a generalized graph illustrating a single nerve fiber firing.
Figure 6:
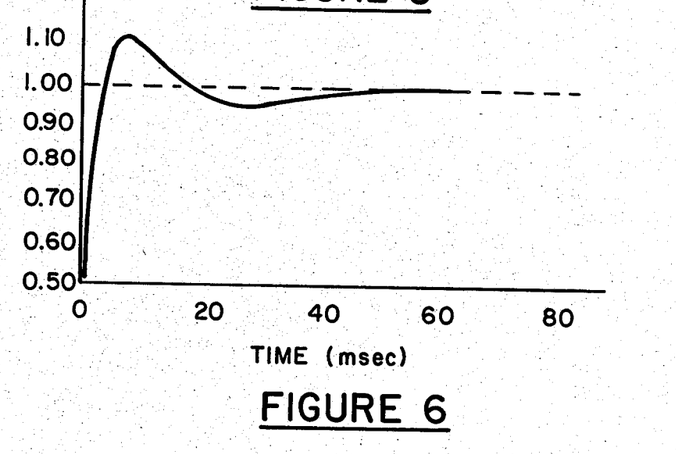
FIG. 6 is a generalized graph illustrating the relative excitability of a neuron with respect to time after firing has occurred.

The electrical activity of nerve fibers can be generalized, for purposes as set forth herein, as shown in the graphs of FIGS. 5 and 6. A generalized graph of voltage over time of a single nerve firing is shown in FIG. 5. It should be noted that the graph is drawn with voltage increasingly negative as it is drawn upward on the graph, as is the custom in neuroscience.

The various depicted portions of the graph of FIG. 5 which are considered important to understanding the invention are as follows:

Action Potential is the firing of the neuron caused by either natural or artificial stimulation of the nerve;

Absolute Refractory Period is a period of time when the nerve cannot be caused to fire (i.e., to produce a second pulse), regardless of how strongly it is stimulated, and this period of time sets the upper limit on the frequency or the rate that the neuron can fire; and Relative Refractory Period is a period of time wherein a stronger than normal stimulus is required to fire, or excite, the nerve, with the strength or intensity of the stimulus required to stimulate the nerve fiber diminishing over time until it reaches a minimum when the fiber has reached its resting potential, and the relative refractory period can contribute to setting the upper limit of the expectation (firing) rate of the neuron, depending upon stimulus intensity.

FIG. 6 depicts a graph of the relative excitability of the A alpha motor neuron (i.e., ease with which the neuron can be stimulated to fire) with respect to time after a previous action potential (firing). It should be noted that the peak occurs at about 6 msec when the fiber is hyperexcitable (i.e., refires or produces a second action potential with the least stimulus).

Neurons may be classified by their fiber diameters and the activity for which they are responsible. When so classified, six basic groups are preferably formed (other groupings are occasionally used, but this grouping is convenient for understanding the invention). The time length which the neuron remains within the periods graphed in FIGS. 5 and 6 are different for each class of neurons. The fiber class, specific function, size diameter, conduction velocity (CV), refractory period time (RP), and peak hyperexcitability time (HE) for five groups are set forth in Table I as follows:

TABLE I
NERVE FIBER CHARACTERISTICS

| | FIBER CLASS | | | |
|---|---|---|---|---|
| | A alpha | A beta | A gamma | C |
| Function | MOTOR FAST TWITCH | MOTOR MEDIUM TWITCH | SENSORY | MOTOR SLOW TWITCH | PAIN & AUTONOMIC |
| SIZE DIA. (MICROMETERS) | 17 | 15 | 13 | 8 | <1.3 |
| CV M/SEC | 80-90 | 60-70 | 50-60 | 10-40 | .7-2.3 |
| RP | .12 MSEC | .5 MSEC | .6 MSEC | 1.1 MSEC | 1.8 MSEC |
| HE | 2 MSEC | 2.5 MSEC | 2.5 MSEC | 4 MSEC | 4.5 MSEC |

Nerves contain a mixture of the above-listed fibers with large numbers of each type of fiber being normally included in the nerve. The effect of electrical stimulation is increased by increasing the frequency with which the stimulus is able to fire the individual fibers (as noted previously) as well as increasing the total number of individual fibers of the same class which are excited simultaneously.

For a more complete explanation of the foregoing, the following references can be utilized: Roger Warwick and Peter L. Williams, GRAY'S ANATOMY, 35th British Edition (Philadelphia: W. B. Saunders Company), multiple citations: Verrnon B. Mountcastle, MEDICAL PHYSIOLOGY, 14th ed. (St. Louis, Toronto, London: The C. V. Mosby Company), vol 1 and 2, multiple citations; and Percival P. Newman, NEUROPHYSIOLOGY, (New York: SP Medical & Scientific Books) multiple citations.

This invention utilizes the foregoing to enhance and optimize the therapeutic benefit of electrical stimulation. For simplicity of explanation, the invention is described hereinafter with respect to application to a particular type of nerve fiber (sensory) to produce maximum sensation (i.e., to stimulate sensory neurons) and is to be considered as an example of the overall invention. Every other type of neuron is susceptible to the same factors (as set forth hereinafter) except that the time periods are different (but still specific) for each class of neuron.

The important factors and their apparent result on the sensory neurons are as follows:

(1) A positive pulse applied to the nerve is believed to set the nerve fibers of the sensory neurons into a condition similar to the refractory period (this pulse is important because it apparently causes a large number of fibers to be synchronized at the same time into the same state or period, thereby causing them to return to the hyperexcitability condition simultaneously);

(2) A negative pulse thereafter applied to the nerve 600 microseconds (plus or minus 50 microseconds) later excites the nerve fibers of the sensory neurons (a negative pulse has been found to provide better stimulation of the action potential, and the negative pulse is timed to arrive just as the sensory fibers leave the refractory period so that the time interval between the pulses of the pulse pair is therefore the same as the time interval of the refractory period—if applied earlier, fewer sensory fibers are excited because they are in the relative refractory period and, therefore, are harder to excite);

(3) A positive pulse (of the next pulse pair) applied to the nerve 2500 microseconds (plus or minus 300 microseconds) after the first positive pulse is believed to again set the nerve fibers of the sensory neurons into a condition similar to the refractory period (this time interval coincides with both the maximum firing rate of a neuron and the time of peak relative excitability and establishes the maximum frequency of repetition);

(4) The width of the pulses is maximized at 50 microseconds (plus or minus 15 microseconds) with the pulse shape or waveform (for example, rise time and or fall time) being unimportant, and pulse amplitude and duration being preferably the same for both the positive and negative pulses of the pulse pair with no improvement in the effect of electrical stimulation being noted when made different.

Figure 7:
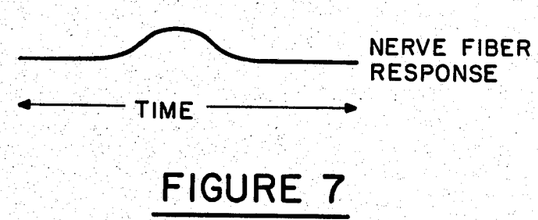
FIG. 7 is a typical bell shaped curve depicting the electrical stimulation effects on a typical nerve fiber.
Figure 8:
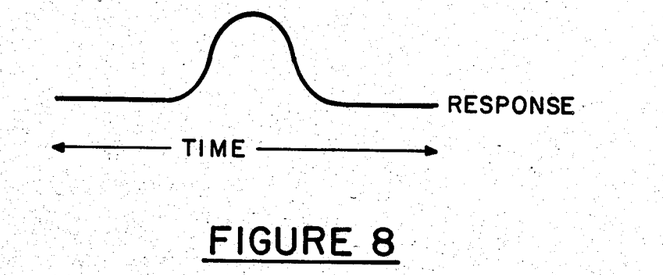
FIG. 8 is a typical bell shaped curve depicting the cumulative effect of frequency and pulse duration on the stimulating effect shown in FIG. 7.

As each factor (listed hereinabove) is adjusted through the time period specified, an apparent bell shaped increase occurs in the effect of the electrical stimulation produced. This effect is very pronounced for each factor and is cumulative as each factor is added. A graph of the apparent effects and resulting stimulation are shown typically in FIGS. 7 and 8.

Pulses of either positive or negative polarity can be inserted between the paired pulses described above without varying the increased effect noted when the pulses of the pulse pair are applied in proper polarity at the proper time intervals as brought out hereinabove. Such additional pulses do not affect the increased stimulation (including the enhanced stimulation as above described) unless included close in time to the second pulse of the pulse pair, in which case they arrive during the relative refractory period and, apparently then reduce the synchronization of the fibers. This result is predictable because nerve fibers in the absolute refractory period cannot be affected by stimulus of any magnitude insufficient to damage the neuron.

Similar but different time dependent factors are described for each class of fibers. For example, the time periods as set forth above for listed factors 2 through 4, are, respectively, 120 microseconds (plus or minus 20 microseconds), 2,000 microseconds (plus or minus 300 microseconds) and 50 microseconds (plus or minus 15 microseconds) for fast twitch motor nerves, and are, respectively, 1,800 microseconds (plus or minus 300 microseconds) 4,500 microseconds (plus or minus 600 microseconds) and 50 microseconds (plus or minus 15 microseconds) for pain reduction neurons.

It should be noted from Table I above that each class of nerve fibers has a range of fiber diameters, and since the time periods of the nerve action potential sequence is dependent upon fiber diameter, a slight modification of time between pulses by modulating the time between pulses and rate will optimally excite still more fibers in a given class of neurons.

Apparatus for achieving interleaved bi-phased pulses to effect optimized stimulation of a plurality of nerve fibers is shown in FIG. 9. As shown, apparatus 54 is similar to that of the apparatus shown in FIG. 1, except that the Q output of one shot multivibrator 26 is coupled through isolation diode 56 to amplifier 28, and the $\overline{Q}$ output of multivibrator 26 is coupled to one shot multivibrator 58 with a leading edge of this input signal to multivibrator 58 triggering the multivibrator. The Q output from one shot multivibrator 58 is applied to one shot multivibrator 60 with a trailing edge of the input triggering multivibrator 60. The Q output of multivibrator 60 is then coupled through isolation diode 62 to amplifier 28, and the input of amplifier 28 is also connected with ground through resistor 64, as indicated in FIG. 9.

Figure 10:
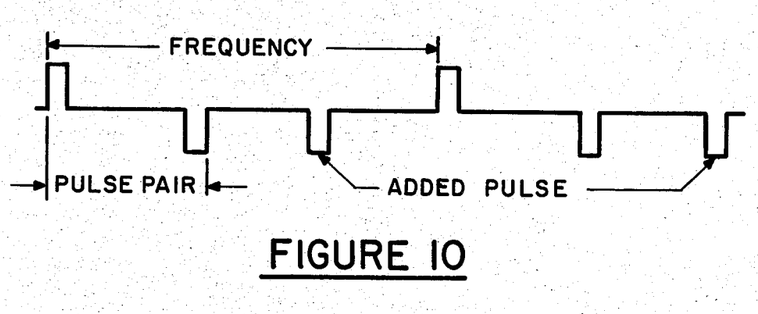
FIG. 10 is a typical representation of interleaved pulse pairs useful to stimulate a plurality of different types of nerve fibers.

This results in a series of pulses being produced at the output of the device (i.e., at secondary winding 30 which is connected with electrodes 31 and 32 as indicated in FIG. 9), which pulses constitute a plurality of pulse pairs (each of which pairs includes the positive pulse and one negative pulse) that are interleaved, as shown in FIG. 10.

Thus, for example, a first pulse pair consists of the positive pulse and the first to occur negative pulse, as shown in FIG. 10, and these pulses are spaced, in time, a distance equal to the refractory period of a first preselected group of nerve fibers, while a second pulse pair consists of the positive pulse and the second to occur negative pulse, as shown in FIG. 10, and these pulses are spaced, in time, a distance equal to the refractory period of a second preselected group of nerve fibers.

If the first selected nerve fibers are, for example, motor nerve fibers, and the second preselected nerve fibers are sensory neurons, then the postive pulse and the first occurring negative pulse are separated, in time, a distance of about 120 microseconds, while the positive pulse and the second occurring negative pulse are separated, in time, a distance of about 600 microseconds to meet the refractory period spacings needed to optimize stimulation of both groups of nerve fibers.

While not specifically shown, it should also be realized that additional pulse pairs could be provided in the same manner as set forth hereinabove so that additional groups of selected nerve fibers can also be simultaneously optimally stimulated.

In operation, the device and method of this invention has been found to be useful in connection with human subjects. Thirty six normal subjects and two chronic pain patients were studied to determine the effects of an electrical waveform which was designed to optimize the effects of stimulation on specific neuronal fibers. The waveform was adjusted to apply electrical pulses of the correct polarity, timed to the refractory period of specific nerve fibers. Substantial increases in the effect of electrical stimulation of sensory, motor (A alpha, beta, and gamma) and pain control fibers (apparently C fibers) was noted. Facilitative stimulation of small diameter nerve fibers has also been demonstrated to manage pain in two patients with chronic cervical, back and head pain.

Twenty three females and thirteen males were tested for subjective assessment of optimal time periods for time between pulses, pulse repetition rate, and pulse width in accordance with this invention. All twenty three females reported cumulative peaking in the effects of electrical stimulation of all three variables.

One male subject did not find a peaking effect for time between pulses for cutaneous sensory fibers. No attempt was made to locate maxima for the other two time dependent variables with this individual because the subject was obviously uncomfortable with the electrical sensation. This individual did produce results consistent with the group for motor fibers. One other male subject was unable to detect a peaking effect associated with time between pulses for motor fibers. This individual produced results for all other parameters which were consistent with the group.

The peaking effects for time between pulses and rate were substantially equal to the refractory period and the maximum firing rate of the selected fibers, respectively. The peaking effect produced by optimum pulse width was extremely consistent in the experimental group and was the same independent of the nerve fiber stimulated. The reason for the peak associated with pulse width is unknown. Results were, however, consistent between individuals.

The two chronic pain patients have retested several times when their pain returned. During each test an effort was made to determine optimum time periods for each variable for pain relief. Thus far, these time periods appear to equal the refractory period (1.8 milliseconds) for small diameter fibers. It should be remembered that the stimulation is facilitative and since the stimulus is almost imperceptible it seems clear that the fibers stimulated are not pain fibers. After each test the pain patients report that they are virtually pain free for two to four days.

As can be appreciated from the foregoing, this invention provides improved apparatus and method for achieving optimization of electrical stimulation of nerve fibers of the human body.

What is claimed is:

1. A method for optimizing electrical stimulation of nerve fibers having predetermined refractory periods and enhanced excitability conditions that occur during known periods following the occurrence of an action potential, said method comprising:

generating a first pulse of positive polarity and applying said first pulse to nerve fibers to be electrically stimulated to thereby set said fibers;

generating a second pulse of negative polarity and applying said second pulse to said nerve fibers to be electrically stimulated to cause excitation thereof, with said second pulse being generated at a time subsequent to said first pulse that is substantially equal to that of the refractory period for said nerve fibers then to be stimulated; and repeatedly generating said first and second pulses with each occurrence of said first and second pulses being timewise spaced from each adjacent first and second pulses a distance based upon the timewise occurrence of said enhanced excitability condition of said preselected nerve fibers to be stimulated to thereby optimize stimulation of said nerve fibers and substantially increase the activity thereof.

2. The method of claim 1 wherein said nerve fibers then to be stimulated have a maximum hyperexcitability condition, and wherein said first and second pulses are repeatedly generated so that said second pulses occur at a time substantially corresponding to the known time of occurrence of said maximum hyperexcitability condition of said nerve fibers then to be stimulated.

3. The method of claim 1 wherein said method includes generating a plurality of pulses of negative polarity each of which occurs timewise after said first pulse of positive polarity, with the pulses of negative polarity being spaced from one another so that each negative polarity pulse cooperates with said positive polarity pulse to thereby form pulse pairs with each pulse pair being spaced, in time, a distance substantially equal to the refractory period for different ones of different types of nerve fibers to be stimulated, and wherein said pulse pairs are applied to said different types of nerve fibers to thereby simultaneously stimulate a plurality of different types of nerve fibers with at least one of said different types of nerve fibers being optimally stimulated.

4. The method of claim 3 wherein said pulse pairs stimulate at least two of sensory, motor, pain control, and autonomic fibers.

5. A device for providing optimized electrical stimulation to preselected nerve fibers having known refractory periods and enhanced excitability conditions that occur during known periods following the occurrence of an action potential, said device comprising:
generating means for generating a series of pulse pairs with each said pair having first and second pulses of positive and negative polarity, respectively, and with said first pulse occurring timewise before said second pulse, said pulses of each said pulse pair being spaced from one another a distance, in time, substantially equal to that of the known refractory period of said preselected nerve fibers to be stimulated, and each pulse pair of said series of pulse pairs occurring so as to be timewise spaced from each adjacent pulse pair a distance based upon the timewise occurrence of said enhanced excitability condition of said preselected nerve fibers to be stimulated; and
application means connected with said generating means and adapted to apply said series of pulse pairs to said preselected nerve fibers so that said first pulse of each said pulse pair sets said preselected nerve fibers, and so that said second pulse of each said pulse pair occurs substantially at the end of said refractory period to excite said preselected nerve fibers, whereby said applied pulse pairs optimize stimulation of said preselected nerve fibers and thereby substantially increase the activity thereof.

6. The device of claim 5 wherein said preselected nerve fibers have a maximum hyperexcitability condition, and wherein said generating means includes means to provide said series of pulse pairs by repeatedly generating said first and second pulses so that said second pulses occur at a time substantially corresponding to the known time of occurrence of said maximum hyperexcitability condition of said preselected nerve fibers.

7. The device of claim 1 wherein said application means includes electrodes adapted to be placed contiguous to said nerve fibers for applying said pulses thereto.

8. The device of claim 7 wherein said device includes switching means to switch polarity sequences between said electrodes to achieve optimum stimulation alternately through said electrodes.

9. The device of claim 5 wherein said generating means includes means providing for stimulation of at least one class of sensory, motor, pain control and autonomic nerve fibers.

10. The device of claim 5 wherein said generating means includes means providing for stimulation of sensory neurons by causing said second pulse to occur between about 550 and 650 microseconds after said first pulse.

11. The device of claim 10 wherein said generating means includes means for causing said second pulse to occur about 600 microseconds after said first pulse.

12. The device of claim 10 wherein said generating means includes means for causing said first and second pulses to be repeated at time intervals such that said second pulses are spaced between about 2200 to 2800 microseconds.

13. The device of claim 10 wherein said generating means includes means for causing said first and second pulses to be repeated at time intervals such that said second pulses are spaced about 2500 microseconds.

14. The device of claim 5 wherein said generating means includes means providing for stimulation of pain reduction neurons by causing said second pulse to occur between about 1500 and 2100 microseconds after said first pulse.

15. The device of claim 14 wherein said generating means includes means for causing said second pulse to occur about 1800 microseconds after said first pulse.

16. The device of claim 14 wherein said generating means includes means for causing said first and second pulses to be repeated at time intervals such that said second pulses are spaced between about 4200 to 4800 microseconds.

17. The device of claim 14 wherein said generating means includes means for causing said first and second pulses to be repeated at time intervals such that said second pulses are spaced about 4500 microseconds.

18. The device of claim 5 wherein said generating means includes means providing for stimulation of fast twitch motor nerves by causing said second pulse to occur between 100 microseconds and 140 microseconds after said first pulse.

19. The device of claim 18 wherein said generating means includes means for causing said second pulse to occur about 120 microseconds after said first pulse.

20. The device of claim 18 wherein said generating means includes means for causing said first and second pulses to be repeated at time intervals such that said second pulses are spaced between 1700 to 2300 microseconds.

21. The device of claim 18 wherein said generating means includes means for causing said first and second pulses to be repeated at time intervals such that said second pulses are spaced about 2000 microseconds.

22. The device of claim 5 wherein said generating means includes means for causing said first and second pulses to each have a duration of between about 35 and 75 microseconds.

23. The device of claim 5 wherein said generating means includes means for causing said first and second pulses to each have a duration of about 50 microseconds.

24. The device of claim 5 wherein said generating means includes means for causing electrical stimulation of a plurality of different types of nerve fibers.

25. A device for providing electrical stimulation to a plurality of nerve fibers having different known refractory periods and enhanced excitability conditions that occur following the occurrence of an action potential, said device comprising:
generating means for generating a series of pulse groups each having first, second and third pulses with said first pulse of each said pulse group being a positive polarity pulse and said second and third pulses of each said pulse group being negative polarity pulses, said first and second pulses of each said pulse group being spaced, in time, from one another a distance substantially equal to the known refractory period of first preselected nerve fibers, said first and third pulses of each said pulse group being spaced, in time, from one another a distance substantially equal to that of the known refractory period of second preselected nerve fibers, said second and third pulses of each said pulse group being also spaced from one another, and each pulse group occurring so as to be timewise spaced from each adjacent pulse group a distance based upon the occurrence of said enhanced excitability condition of one of said first and second preselected nerve fibers to be stimulated; and application means connected with said generating means to receive said pulses therefrom and adapted to apply said pulses to said nerve fibers so that said first pulse of each said pulse group sets said first and second preselected nerve fibers, and so that said second and third pulses of each said pulse group occur substantially at the end of said refractory period for said first and second preselected nerve fibers, respectively, to excite said first and second preselected nerve fibers, whereby said applied pulse groups stimulate both said first and second nerve fibers to increase the activity of both said first and second nerve fibers with at least one of said first and second nerve fibers being optimally stimulated.

* * * * *